(12) United States Patent
Jones et al.

(10) Patent No.: US 7,294,123 B2
(45) Date of Patent: Nov. 13, 2007

(54) ACTIVATABLE BIOACTIVE VASCULAR OCCLUSIVE DEVICE AND METHOD OF USE

(75) Inventors: Donald K. Jones, Lauderhill, FL (US); Juan A. Lorenzo, Davie, FL (US); Mark L. Pomeranz, Davie, FL (US); Darren Sherman, Ft. Lauderdale, FL (US)

(73) Assignee: Corris Neurovascular, Inc., Miami Lakes, FL (US)

( * ) Notice: Subject to any disclaimer, the term of this patent is extended or adjusted under 35 U.S.C. 154(b) by 80 days.

(21) Appl. No.: 10/738,473

(22) Filed: Dec. 17, 2003

(65) Prior Publication Data

US 2005/0149107 A1  Jul. 7, 2005

(51) Int. Cl.
*A61M 31/00* (2006.01)
*A61M 29/00* (2006.01)

(52) U.S. Cl. ..................... 604/508; 606/191

(58) Field of Classification Search ............... 606/191, 606/200, 151, 108, 213, 157; 604/285–288, 604/265, 891.1, 500, 507, 508; 623/1.42–1.48; 424/422–425
See application file for complete search history.

(56) References Cited

U.S. PATENT DOCUMENTS

| | | | |
|---|---|---|---|
| 4,994,069 A | 2/1991 | Ritchart et al. | |
| 5,108,407 A | 4/1992 | Geremia et al. | |
| 5,122,136 A | 6/1992 | Guglielmi et al. | |
| 5,226,911 A | 7/1993 | Chee et al. | |
| 5,304,194 A | 4/1994 | Chee et al. | |
| 5,334,210 A | 8/1994 | Gianturco | |
| 5,366,454 A * | 11/1994 | Currie et al. | 604/890.1 |
| 5,382,259 A | 1/1995 | Phelps et al. | |
| 5,639,277 A | 6/1997 | Mariant et al. | |
| 5,658,308 A * | 8/1997 | Snyder | 606/191 |
| 5,669,931 A | 9/1997 | Kupiecki et al. | |
| 5,690,671 A | 11/1997 | McGurk et al. | |
| 5,695,480 A | 12/1997 | Evans et al. | |
| 5,749,894 A | 5/1998 | Engelson | |
| 5,750,585 A | 5/1998 | Park et al. | |
| 5,853,418 A | 12/1998 | Ken et al. | |
| 5,925,062 A | 7/1999 | Purdy | |
| 5,935,145 A | 8/1999 | Villar et al. | |
| 5,976,162 A | 11/1999 | Doan et al. | |
| 5,980,550 A * | 11/1999 | Eder et al. | 606/191 |
| 6,015,424 A * | 1/2000 | Rosenbluth et al. | 606/200 |

(Continued)

FOREIGN PATENT DOCUMENTS

EP  1 369 137 A  12/2003

(Continued)

OTHER PUBLICATIONS

U.S. Appl. No. 10/738,477, Donald K. Jones, et al.

(Continued)

*Primary Examiner*—Catherine S. Williams
(74) *Attorney, Agent, or Firm*—Michael W. Montgomery

(57) ABSTRACT

A vascular occlusive device which includes a support structure and a bioactive coating disposed onto the support structure and an outer barrier coating which serves to prevent a reaction between the bioactive agent and bodily fluids until the outer barrier is activated by applying an external agent to the outer barrier.

3 Claims, 5 Drawing Sheets

U.S. PATENT DOCUMENTS

| | | | |
|---|---|---|---|
| 6,024,754 A * | 2/2000 | Engelson | 606/213 |
| 6,124,131 A | 9/2000 | Semenza | |
| 6,187,024 B1 | 2/2001 | Boock et al. | |
| 6,187,027 B1 | 2/2001 | Mariant et al. | |
| 6,231,590 B1 | 5/2001 | Slaikeu et al. | |
| 6,251,136 B1 * | 6/2001 | Guruwaiya et al. | 623/1.46 |
| 6,280,457 B1 | 8/2001 | Wallace et al. | |
| 6,287,318 B1 | 9/2001 | Villar et al. | |
| 6,299,627 B1 * | 10/2001 | Eder et al. | 606/191 |
| 6,423,085 B1 | 7/2002 | Murayama et al. | |
| 6,425,914 B1 * | 7/2002 | Wallace et al. | 623/1.11 |
| 6,494,884 B2 | 12/2002 | Gifford, III et al. | |
| 6,599,275 B1 | 7/2003 | Fischer, Jr. | |
| 6,602,261 B2 | 8/2003 | Greene, Jr. et al. | |
| 6,602,269 B2 * | 8/2003 | Wallace et al. | 606/191 |
| 6,773,429 B2 * | 8/2004 | Sheppard et al. | 604/891.1 |
| 2002/0004681 A1 | 1/2002 | Teoh et al. | |
| 2002/0049503 A1 | 4/2002 | Milbocker | |
| 2002/0058640 A1 * | 5/2002 | Abrams et al. | 514/44 |
| 2002/0087184 A1 | 7/2002 | Eder et al. | |
| 2002/0120297 A1 | 8/2002 | Shadduck | |
| 2002/0151915 A1 | 10/2002 | Hieshima et al. | |
| 2002/0193823 A1 | 12/2002 | Wallace et al. | |
| 2003/0017190 A1 | 1/2003 | Motasim et al. | |
| 2003/0074049 A1 | 4/2003 | Hoganson et al. | |
| 2003/0093147 A1 | 5/2003 | Ogle et al. | |
| 2004/0029952 A1 * | 2/2004 | Chen et al. | 514/449 |

FOREIGN PATENT DOCUMENTS

| | | |
|---|---|---|
| WO | WO 02/083039 A1 | 10/2002 |
| WO | WO 3092791 A2 * | 11/2003 |

OTHER PUBLICATIONS

U.S. Appl. No. 10/868,152, Donald K. Jones, et al.
U.S. Appl. No. 10/868,303, Donald K. Jones, et al.
U.S. Appl. No. 10/820,967, Juan A. Lorenzo, et al.
Cordis Neurovascular Instructions for Use for Vascular Occlusion System, dated Jan. 2001.

* cited by examiner

ACTIVATABLE BIOACTIVE VASCULAR OCCLUSIVE DEVICE AND METHOD OF USE

BACKGROUND OF INVENTION

1. Field of the Invention

The present invention relates to medical implantable device, and more particularly, to a vascular occlusive device, such as an embolic coil for occluding an aneurysm, which includes a bioactive coating placed on the occlusive device for reacting with bodily tissue in order to promote a desired result, for example promoting an increase of tissue growth into the occlusive device.

2. Description of the Prior Art

For many years vasculature occlusive devices have been placed within the vasculature of the human body to occlude, or partially occlude, blood flow through the vasculature. Additionally, such devices have been introduced into aneurysms in order to fill, or partially fill, the aneurysm so as to reduce the pressure which is applied to the interior of the aneurysm in order to prevent further growth or expansion of the aneurysm. These devices may take the form of a coil, such as a helical coil, and are typically placed within the vessel or aneurysm by use of a delivery catheter which is inserted into the vessel and positioned such that the distal end of the delivery catheter is adjacent to a selected site for placement. Once the occlusive device is placed within a blood vessel or aneurysm, surrounding tissue reacts with the "foreign" object and begins to grow into and around the device to provide more complete occlusion of the vessel.

Examples of such delivery catheters are disclosed in U.S. Pat. No. 5,108,407, entitled "Method And Apparatus For Placement Of An Embolic Coil" and U.S. Pat. No. 5,122,136, entitled "Endovascular Electrolytically Detachable Guidewire Tip For The Electroformation Of Thrombus In Arteries, Veins, Aneurysms, Vascular Malformations And Arteriovenous Fistulas." These patents disclose catheter systems for delivering embolic coils to preselected positions within vessels of the human body in order to treat aneurysms, or alternatively, to occlude a blood vessel at a preselected location.

Occlusive devices which take the form of coils may be helically wound coils, random wound coils, coils wound within coils or other such coil configurations. Examples of various coil configurations are disclosed in U.S. Pat. No. 5,334,210, entitled, "Vascular Occlusion Assembly" and U.S. Pat. No. 5,382,259, entitled, "Vasoocclusion Coil With Attached Tubular Woven Or Braided Fibrous Covering." Such coils are generally formed from radiopaque metallic materials, such as platinum, gold, tungsten or alloys of these metals. Oftentimes several coils are placed at a given location within a vessel, or within an aneurysm, to more completely occlude, or partially occlude, the flow of blood through the vessel or aneurysm. Thrombus growth onto the coils further enhances the occlusive effect of the coils.

In the past, embolic coils have been placed within the distal end of a delivery catheter and when the distal end of the catheter is properly positioned, the coil may then be pushed out of the end of the catheter with, for example a guidewire, to release the coil at the desired location. This procedure of placement of the embolic coil is conducted under fluoroscopic visualization such that the movement of the coil may be monitored and the coil may be placed at a desired location.

In addition, such coils have been specifically designed to be stretch resistant, such as the vasculature occlusive coil disclosed in U.S. Pat. No. 5,853,418, entitled, "Stretch Resistant Vaso-Occlusive Coils (II)" which discloses a helically wound coil having a polymeric stretch resistant member extending through the lumen of the coil and fixedly attached to both ends of the coil to prevent the coil from stretching.

In order to increase the thrombogenicity of an embolic coil, such coils have included a coating, such as collagen, which is applied to the surface of the coil. This concept is disclosed in U.S. Pat. No. 5,690,671, entitled, "Embolic Elements And Methods And Apparatus For Their Delivery," which discloses such a collagen coated embolic coil.

In addition, U.S. Pat. No. 5,980,550, entitled, "Water-Soluble Coating For Bioactive Vasoocclusive Devices," discloses an embolic coil having an inner coating which serves as a thrombogenic agent and an outer coating of a water soluble agent which dissolves after placement of the coil in order expose the thrombogenic inner coating to enhance the growth of thrombus into an around the coil.

The water soluble coating prevents the thrombogenic inner coating from coming into contact with the surrounding blood until the water soluble coating is dissolved by contact with blood which is comprised largely of water.

While the vasculature occlusive device disclosed in this patent includes an agent for enhancing thrombogenicity of the device and also includes an outer coating to prevent such activity until the outer coating is dissolved by blood flow, there is no control over when the dissolving process begins and therefore no control over the time in which the thrombogenic agent becomes activated. Without such control, it is possible that thrombus can begin forming on the coil prior to the time the coil is properly placed within a vessel, or aneurysm, therefore making it very difficult if not impossible to reposition, or remove, the improperly placed coil. Alternatively, with water soluble outer protective coating the passive process of removing the outer coating may be so slow that the reaction may not occur in a timely manner.

SUMMARY OF THE INVENTION

In accordance with one aspect of the present invention, there is provided a vascular occlusive device, such as an embolic coil for treating an aneurysm, which includes a support member which may take the form of a helical coil, a bioactive agent which is disposed on the support member, and an outer barrier which is disposed on the bioactive agent to prevent contact between the bioactive agent and a bodily fluid when the vasculature occlusive device is inserted into a blood vessel or aneurysm. The outer barrier exhibits the characteristic of being inert to bodily fluid, but dissolves upon being exposed to an external agent. The external agent may take the form of a liquid medium which may be injected into the blood vessel or aneurysm.

In accordance with another aspect of the present invention, the bioactive agent takes the form of a coating which is applied to the support member and which serves to enhance a reaction of the body, such as for example the growth of thrombus, into and around the vasculature occlusive device. The outer barrier takes the form of an outer coating applied to the bioactive agent and prevents bodily fluid, such as blood, from reacting with the bioactive agent until such time as the outer barrier is exposed to an external agent. The external agent may take the form of a solvent which when applied to the outer barrier causes the outer barrier to dissolve away from the bioactive agent.

In accordance with still another aspect of the present invention, there is provided an embolic coil for treating an aneurysm which is coated with a thrombogenic agent, or an agent which increases or promotes the growth of thrombus material, and an outer coating applied to the thrombogenic coating which prevents a reaction between blood and the thrombogenic agent until such time as an external agent is applied to the outer coating to thereby cause this coating to dissolve away from the thrombogenic coating.

In accordance with still another aspect of the present invention, there is provided a method for treating an aneurysm which includes the steps of inserting a vascular occlusive device which comprises a support member, a bioactive agent disposed on the support member, and an outer coating disposed on the bioactive agent which outer coating exhibits the characteristic of dissolving to uncover at least a portion of the bioactive agent when an external medium is applied to the outer coating. The method also includes the steps of inserting the vascular occlusive device into a blood vessel, or an aneurysm, and, upon election, applying an external medium to the outer coating to thereby cause the outer coating to dissolve and expose at least a portion, or all, of the bioactive agent to thereby cause a desired reaction between the body and the vascular occlusive device.

In accordance with still another aspect of the present invention, the method includes the steps of providing a vasculature occlusive coil which has a thrombus inducing surface and which is coated with an outer coating which exhibits the characteristics of dissolving to expose at least a portion of the thrombogenic material when an external agent is applied to the outer coating. This method step also includes the steps of inserting the vasculature occlusive device into a blood vessel or an aneurysm, and then upon election, applying an external agent to the outer coating to thereby cause the outer coating to dissolve and expose at least a portion of the thrombogenic surface of the vasculature occlusive device.

DESCRIPTION OF THE PREFERRED EMBODIMENT

Figure 1:
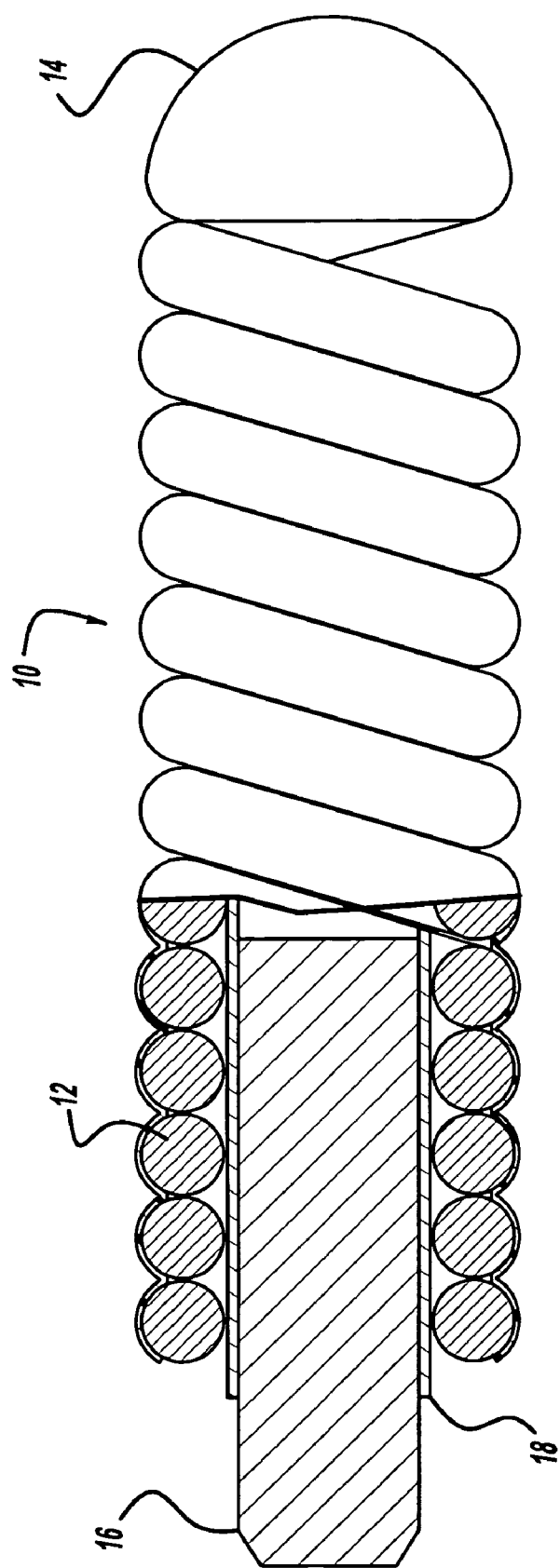
FIG. 1 is an elevational view of an embolic coil illustrating a vascular occlusive coil in accordance with one embodiment of the present invention.
Figure 2:
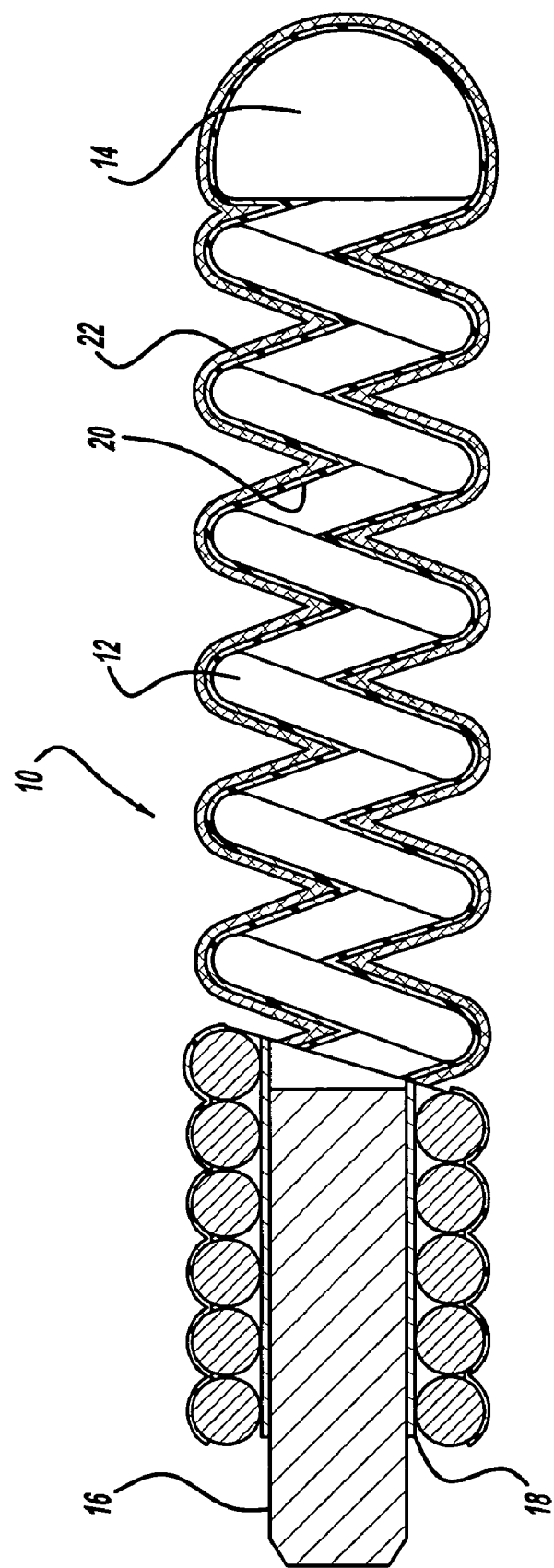
FIG. 2 is an elevational view, partly in cross-section of the vascular occlusive coil as shown in FIG. 1 illustrating a bioactive coating and an outer barrier coating in accordance with the embodiment of the present invention.

FIGS. 1 and 2 illustrate a vascular occlusive device which takes the form of an embolic coil 10 which may be placed along with other similar coils into a blood vessel or into an aneurysm in order to partially fill the aneurysm. More particularly, the embolic coil 10 is a typical embolic coil which comprises a helically wound coil 12 formed from a platinum alloy wire wound into a helical configuration. The diameter of the wire is generally in the range of about 0.0007 inches to about 0.008 inches and the outer diameter of the coil 12 is preferably in a range of about 0.003 inches to about 0.055 inches. While the particular embolic coil 12 illustrated in FIGS. 1 and 2 is shown as being a straight, helically wound coil, it should be appreciated that embolic coils are formed in various configurations and may take the form of a helix, a random shaped configuration or even a coil within a coil.

Preferably the embolic coil 10 includes a weld bead 14 which is attached to the distal end of the coil for providing a less traumatic distal end for the embolic coil 10. In addition, the embolic coil 10 includes a cylindrical headpiece 16 which is placed into the lumen of the helically wound coil 12 at the proximal end of the coil and is held in place by an adhesive material 18 interposed between the cylindrical headpiece 16 and the helical coil 12. The construction of the embolic coil 10 and an associated hydraulic deployment system for placing the embolic coil within an aneurysm is disclosed in more detail in U.S. patent application Ser. No. 10/102,154, entitled, "Small Diameter Embolic Coil Hydraulic Deployment System," filed Mar. 19, 2002, assigned to the same assignee of the present invention and is hereby incorporated by reference.

FIG. 2 illustrates in more detail a bioactive agent 20, and an outer barrier 22 which is disposed upon the bioactive agent 20 for preventing the activation of the bioactive agent until such time as an election is made to activate the bioactive agent. More particularly, the bioactive agent 20, which may take the form of a thrombogenic agent, i.e. an agent which serves to increase or promote the growth and adhesion of thrombus onto the surface of the embolic coil 10, is coated onto the outer surface of the coil 12. While the bioactive agent may take the form of a thrombogenic agent, it should be understood that the bioactive agent may take any form which would induce a desired reaction bodily tissue. For example, the bioactive agent may serve to cause blood to clot onto the surface of the embolic coil 10, it may serve to enhance the adhesion of thrombus onto the surface of the embolic coil, or it may serve to cause adjacent embolic coils to become bonded to each other through adhesion by components of blood. It should be appreciated that there are many other reactions which might exist between the bioactive agent and bodily tissue which would be desirable.

The outer barrier 22 takes the form of a coating which is disposed upon the bioactive agent 20 and serves to insulate the bioactive agent from adjacent bodily fluid until such time as a decision is made by a physician to activate the outer barrier 22. The outer barrier 22 takes the form of a material which is inert to bodily fluid, but which dissolves and exposes the bioactive agent 20 when the outer barrier 22 is subjected to an external agent.

In a preferred embodiment, the bioactive agent 20 is comprised of polyglycolic acid, the outer barrier 22 is comprised of ethylene vinyl alcohol and the external agent for dissolving the outer barrier 22 is dimethyl sulfoxide (DMSO) which serves to dissolve the outer barrier 22 to thereby expose the bioactive agent 20.

It should be appreciated that there are numerous materials which would serve as a bioactive agent, an outer barrier and an external agent, some of which are indicated hereinafter. It is important, however, that the external agent be inert to bodily fluids, such as being non-water soluble, such as blood, in order to prevent the outer barrier 22 from dissolving and exposing the bioactive agent 20 until such time as an election is made by a physician to activate the outer barrier 22.

Figure 3A:
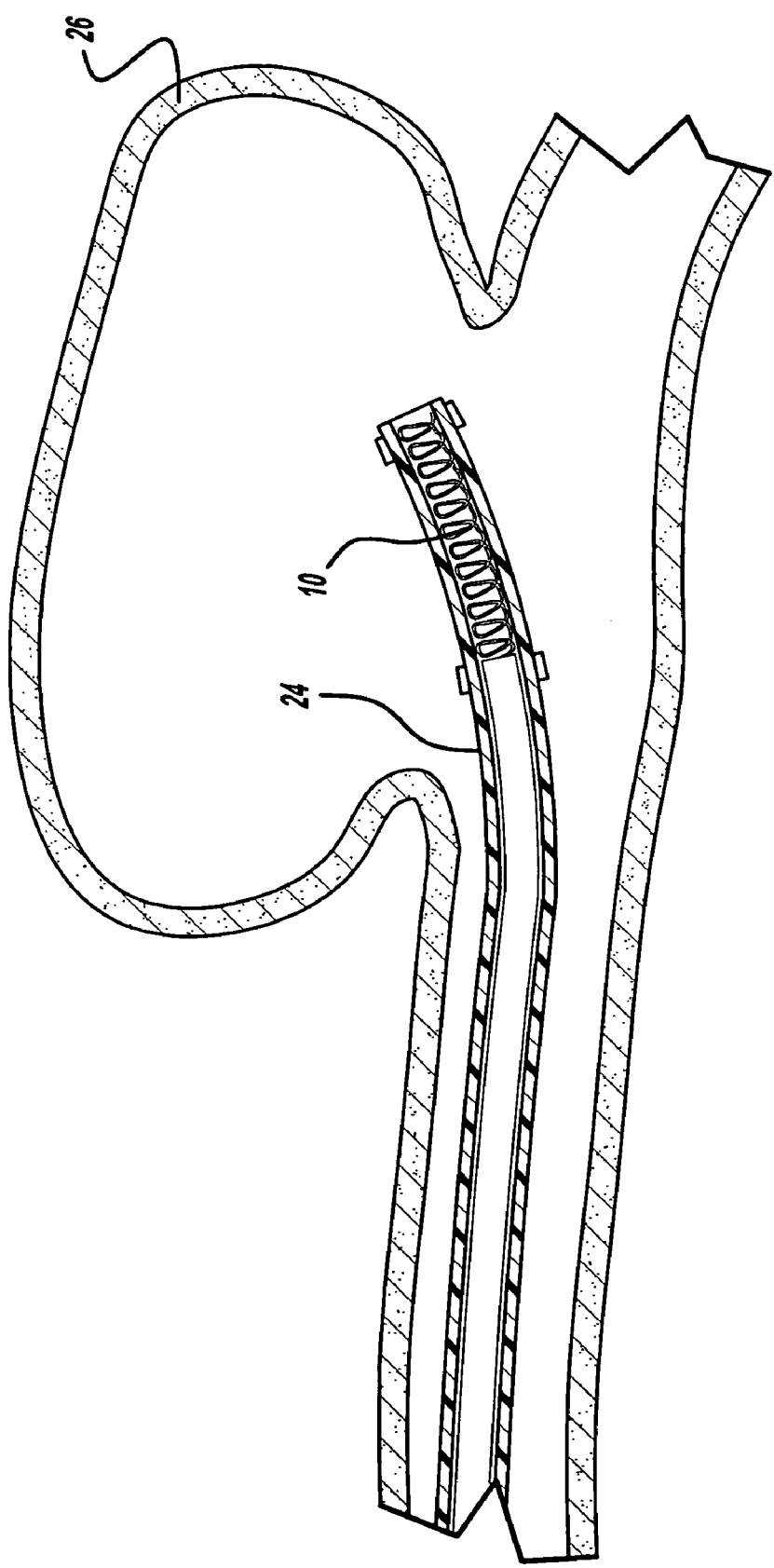
FIGS. 3A through 3C illustrate the method steps of applying multiple vascular occlusive coils as shown in FIG. 1 into an aneurysm and thereafter applying an external agent to thereby activate the embolic coils.
Figure 3B:
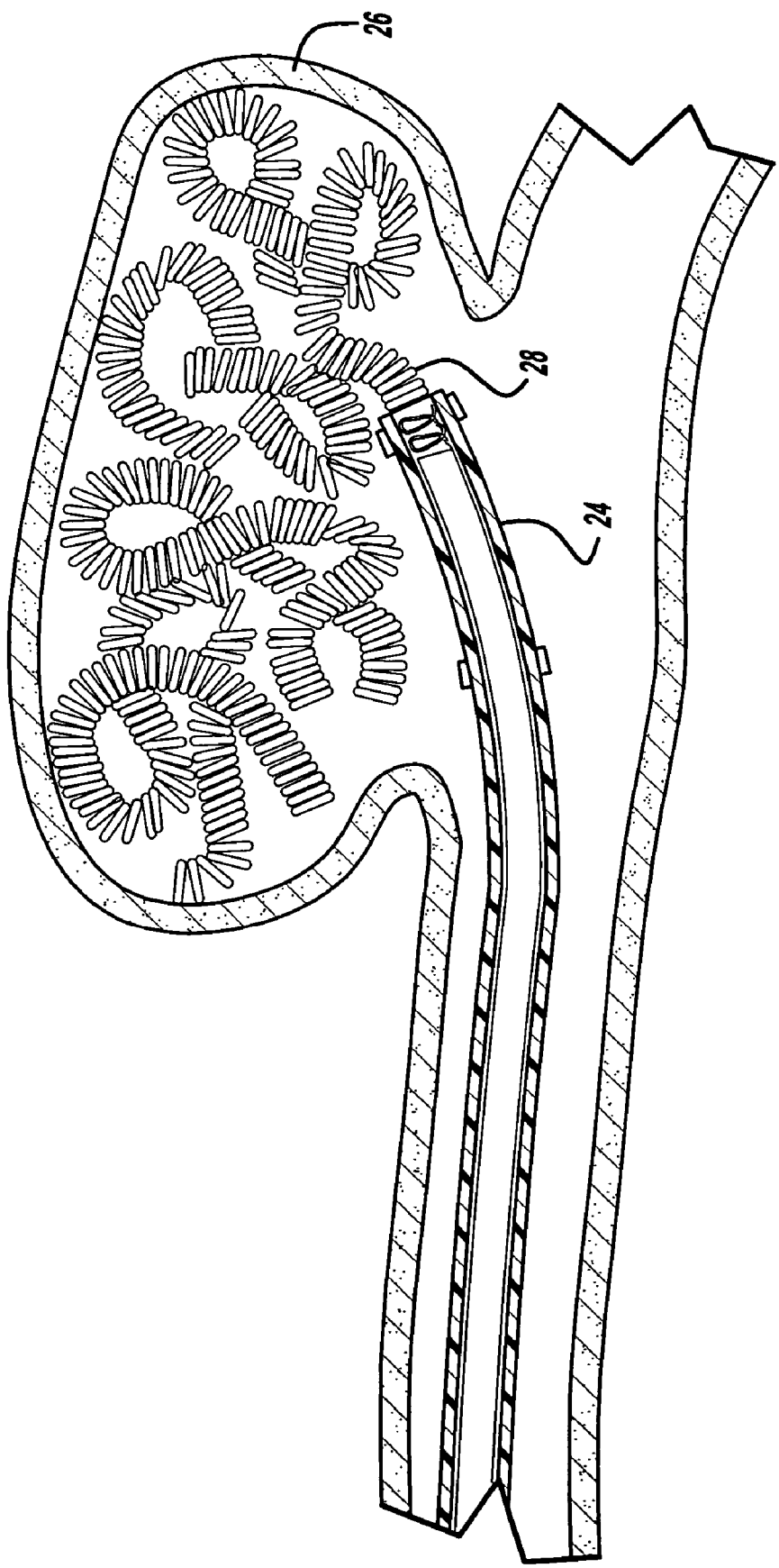
Figure 3C:
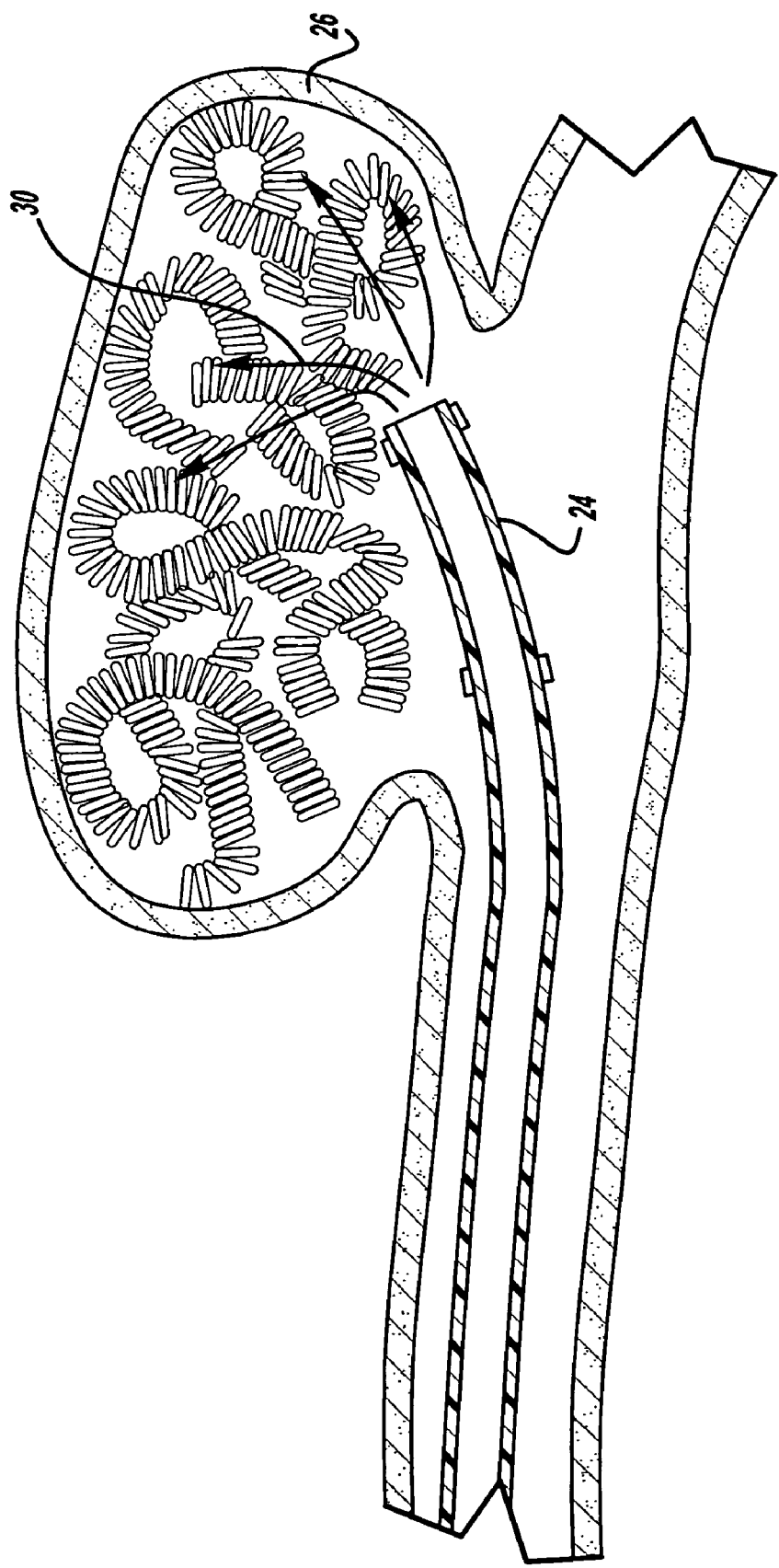

FIGS. 3A through 3C generally illustrate a method of utilizing the present invention. More particularly, FIG. 3A illustrates a delivery catheter 24 having an embolic coil 10 placed in the distal end of the catheter for delivery into an aneurysm 26. FIG. 3B illustrates the delivery catheter 24 being used to position multiple vascular occlusive coils including a final embolic coil 28 into the aneurysm 26. FIG. 3C illustrates the application of an external agent 30, which may take the form of a solvent for dissolving the outer barrier 22 to thereby activate the outer barrier 22 to expose at least a portion of the bioactive agent 20.

It may be desirable to place all of the vascular occlusive coils into the aneurysm 26 prior to applying the external agent 30, however, another approach is that of placing a single coil into the aneurysm and thereafter activating that single coil, placing a second coil into the aneurysm and thereafter activating the second coil and so forth until all of the coils have been properly placed into the aneurysm. As may be appreciated, the advantage of the subject invention over prior devices is that the physician may determine at what point in time during the process of "filling" an aneurysm the physician elects to activate a coil as opposed to having no control over the time in which the coils become activated.

The bioactive agent may take the form of any material or surface which when placed into the body causes or inhibits a reaction with a bodily substance. For example, the bioactive agent may be a thrombus inducing material, or surface when placed within a blood vessel induces the growth of thrombus onto the surface of the bioactive agent or where the bioactive agent is a thrombolitic agent to inhibit the growth of tissue. The bioactive agent could take the form of a material which causes blood to clot onto the surface of the material, a material which produces an immune response, a material which releases a human growth factor, a material which promotes endothelization, etcetera. Another example of a bioactive agent is a pharmacologic agent which is inactive until the barrier is dissolved, or removed, or is modified, by an external source to expose the pharmacological agent to the body. A preferred bioactive agent to be used with a vascular occlusive coil is polyglycolic acid which promotes the growth of tissue.

The outer barrier may take the form of a coating applied to the bioactive agent, or a substance added to the bioactive agent, which causes the bioactive agent to be substantially non-reactive with bodily fluids until such time as the outer barrier is acted upon by an external agent. A preferred outer barrier to be used with a vascular occlusive coil is a coating of ethylene vinyl alcohol which serves to encase the bioactive agent until a solvent is applied to the coating to thereby dissolve, or remove, or modify the barrier in order to expose the bioactive agent to the body.

The external agent may take the form of any agent which when applied to the outer barrier causes the outer barrier to become ineffective in preventing a reaction between the bioactive agent and bodily tissue. The external agent may take the form of a solvent for dissolving the outer barrier in order to expose the bioactive agent, or it may take the form of a substance which reacts with the bioactive agent in order to activate the bioactive agent. The external agent may for example be a liquid material or it may be a source of heat or a laser source for dissolving the outer barrier, or removing all or part of the outer barrier or for modifying the outer barrier such as for example biologically modifying the outer barrier in order to activate receptors of the bioactive agent, in order to expose the bioactive agent to bodily tissue. A preferred external agent for a vascular occlusive coil is dimethyl sulfoxide which serves as a solvent to dissolve an outer barrier coating comprising ethylene vinyl alcohol so as to permit the bioactive agent to come into contact with bodily tissue. By "bodily tissue" is meant any substance within the human body and includes blood, fibrous growth within blood vessels, etcetera.

Although a preferred embodiment of the present invention has been described, it is to be understood that various modifications may be made by those skilled in the art without departing from the scope of the claims which follow.

That which is claimed is:

1. A method of treating an aneurysm comprising the steps of:
   providing a vascular occlusive device comprising a support member, a bioactive agent disposed on said support member, and a barrier exhibiting the characteristics of normally preventing a reaction between the bioactive agent and a bodily fluid and of exposing a portion of said bioactive agent when an external agent is applied to said barrier;
   inserting a delivery catheter into a blood vessel;
   advancing the distal tip of the delivery catheter through the blood vessel until the distal tip is adjacent an aneurysm within the blood vessel;
   delivering said vascular occlusive device with the delivery catheter into an aneurysm; and,
   applying said external agent through the catheter and into the aneurysm to thereby activate said barrier to expose said bioactive agent to bodily tissue to thereby cause a reaction between the bioactive agent and the bodily tissue.

2. A method of treating an aneurysm comprising the steps of:
   providing a vascular occlusive device comprising a support member having a bioactive surface which reacts with bodily tissue and having a barrier which exhibits the characteristic of normally inhibiting a reaction between said bioactive surface of said vascular occlusive device and bodily tissue;
   inserting a delivery catheter into a blood vessel;
   advancing the distal tip of the delivery catheter through the blood vessel until the distal tip is adjacent an aneurysm with the blood vessel;
   delivering said vascular occlusive device with the delivery catheter into an aneurysm; and,
   applying an external agent through the catheter and into the aneurysm to thereby activate said barrier and thus expose said bioactive surface to bodily tissue to thereby cause a reaction between the bioactive surface and the bodily tissue.

3. A method of delivering a bioactive agent to a desired location in a blood vessel comprising the steps of:
   providing a support member having a bioactive surface which reacts with bodily tissue and having a barrier which exhibits the characteristic of normally inhibiting a reaction between said bioactive surface of said support member and bodily tissue;
   inserting a delivery catheter into a blood vessel;
   advancing the distal tip of the delivery catheter through the blood vessel until the distal tip is adjacent the desired location within the blood vessel;
   delivering said support member with the delivery catheter to the desired location; and,
   applying an external agent through the catheter to said support member to thereby activate said barrier and thus expose said bioactive surface to bodily tissue to thereby cause a reaction between the bioactive surface and bodily tissue.

* * * * *

UNITED STATES PATENT AND TRADEMARK OFFICE
CERTIFICATE OF CORRECTION

PATENT NO. : 7,294,123 B2  Page 1 of 1
APPLICATION NO. : 10/738473
DATED : November 13, 2007
INVENTOR(S) : Jones et al.

It is certified that error appears in the above-identified patent and that said Letters Patent is hereby corrected as shown below:

Title Page

(73) Assignee: Corris Neurovascular, Inc., Miami Lakes, FL (US)

SHOULD READ

(73) Assignee: Cordis Neurovascular, Inc. Miami Lakes, FL (US)

Signed and Sealed this

First Day of April, 2008

JON W. DUDAS
*Director of the United States Patent and Trademark Office*